United States Patent
Obana

(10) Patent No.: US 7,338,813 B2
(45) Date of Patent: Mar. 4, 2008

(54) CARRIER PARTICLE LATEX FOR ASSAY REAGENT AND ASSAY REAGENT

(75) Inventor: Satoshi Obana, Mishima-gun (JP)

(73) Assignee: Sekisui Chemical Co., Ltd., Osaka (JP)

( * ) Notice: Subject to any disclaimer, the term of this patent is extended or adjusted under 35 U.S.C. 154(b) by 579 days.

(21) Appl. No.: 10/482,302

(22) PCT Filed: Jul. 2, 2002

(86) PCT No.: PCT/JP02/06669

§ 371 (c)(1),
(2), (4) Date: Apr. 16, 2004

(87) PCT Pub. No.: WO03/005031

PCT Pub. Date: Jan. 16, 2003

(65) Prior Publication Data

US 2004/0171176 A1    Sep. 2, 2004

(30) Foreign Application Priority Data

| Jul. 2, 2001 | (JP) | ............................. 2001-201119 |
| Sep. 11, 2001 | (JP) | ............................. 2001-275229 |
| Feb. 26, 2002 | (JP) | ............................. 2002-049957 |

(51) Int. Cl.
    *G01N 33/545* (2006.01)
(52) U.S. Cl. ...................... 436/531; 428/403; 436/532; 436/533; 436/534
(58) Field of Classification Search ...................... None
    See application file for complete search history.

(56) References Cited

U.S. PATENT DOCUMENTS

| 4,305,925 A | 12/1981 | Kapmeyer et al. |
| 4,605,686 A | 8/1986 | Obana et al. |

FOREIGN PATENT DOCUMENTS

| EP | 0 263 731 A | 4/1988 |
| EP | 0 308 233 A | 3/1989 |
| EP | 0 898 169 A | 2/1999 |
| JP | 55131008 B2 | 10/1980 |
| JP | 63014783 B2 | 11/1980 |
| JP | 58198508 B2 | 11/1983 |
| JP | 63065369 A | 3/1988 |
| JP | 63065369 B2 | 3/1988 |
| JP | 5018973 A | 1/1993 |
| JP | 10-48215 A | 2/1998 |
| JP | 10048215 A | 2/1998 |
| JP | 2000-355553 A | 12/2000 |
| JP | 2000355553 A | 12/2000 |

OTHER PUBLICATIONS

Patent Abstracts of Japan, vol. 010, No. 043, Feb. 20, 1986, JP 60-192706A, Sekisui Kagaku Kogyo KK.
Patent Abstracts of Japan, vol. 006, No. 233, Nov. 19, 1982, JP 57-135361A, Sekisui Kagaku Kogyo KK.

*Primary Examiner*—Christopher L. Chin
(74) *Attorney, Agent, or Firm*—Sughrue Mion, PLLC

(57) ABSTRACT

An objective of the invention is to provide a carrier particle latex for an assay reagent capable of assaying a biological sample at a wide range of the concentration in an immunoserological test and capable of being stored stably for a prolonged period, as well as an assay reagent employing the same.

The invention is a carrier particle latex for an assay reagent comprising a carrier particle comprising a copolymer of a polymerizable monomer having a phenyl group and a polymerizable monomer having a phenyl group and a sulfonate, wherein said carrier particle has a surface sulfonic acid group amount of 0.005 to 0.7 $\mu mol/m^2$ and an average particle size of 0.01 to 1.5 μm.

4 Claims, 6 Drawing Sheets

CARRIER PARTICLE LATEX FOR ASSAY REAGENT AND ASSAY REAGENT

TECHNICAL FIELD

The present invention relates to a carrier particle latex for an assay reagent capable of assaying a biological sample at a wide range of the concentration in an immunoserological test and capable of being stored stably for a prolonged period, and an assay reagent employing the same.

BACKGROUND ART

In the field of clinical laboratory tests, various diseases are diagnosed using biological samples (blood, urine and the like), and as methods for diagnosing them various assay methods have been developed and utilized. Representatives of such assay methods are biochemical assay methods utilizing enzymatic reactions and immunological assay methods utilizing antigen-antibody reactions. As reagents employed in such diagnoses, those relating to a pregnancy test, RA test for detecting a rheumatoid factor, CRP test for detecting a C-reactive protein, as well as tests for hepatitis B surface antigen (HBs antigen), anti-HBs antibody, β2 microglobulin antibody, mycoplasma antigen, nucleic acids, nucleic proteins, estrogen, anti-estrogen antibody and the like have been developed.

As such assay methods, an immunonephelometry (TIA method), latex nephelometry (LIA method), enzyme immunoassay (EIA method) and radioimmunosassay (RIA method) may be exemplified, and are selected appropriately depending on the purpose.

Among those listed above, an LIA method is applied to the detection of various antigens and antibodies since it is convenient and can rapidly be conducted, in which a latex carrier particle formed by dispersing a carrier particle in an aqueous medium is sensitized with an antigen or an antibody, and then used to detect the reaction with a corresponding antibody or antigen in serum as an aggregation reaction of the carrier particle.

A recent trend in medical practices is a change from a conventional diagnosis of a disease to a prophylaxis of a disease. Thus, by means of a test of a blood and the like prior to the onset of a disease, the predisposition of the disease is identified beforehand, whereby effecting the prophylaxis. For the purpose of application of such preventive medical cares, a further higher sensitivity is demanded in performing the LIA method and the like. While an immunoserological test such as an antigen-antibody reaction originally assays a small amount of a substance, a reagent for the assay used in the prophylactic medicine should be capable of detecting a disease-associated trace protein (antigen and/or antibody) at a further lower concentration. Thus, an assay reagent which is even more sensitive than those employed currently becomes essential.

In view of the problems discussed above, an instrument of automatic immunological analysis instrument used for immunological tests to assay a small amount of a sample and a small amount of a reagent has increasingly been improved, and correspondingly raised a demand for a higher sensitivity of the reagent employed in such an instrument.

As a method for increasing the sensitivity of such a reagent, a method is exemplified in which an analyze is attempted to be assayed at a higher sensitivity by increasing the particle size of a carrier particle employed whereby increasing the magnitude of the change of optical density. Japanese Kokoku Publication Sho-58-50645 discloses a method for producing a latex which comprises copolymerizing styrene with a styrene sulfonate in an amount of 10% by weight or less based on said styrene in water using a persulfate as an initiator in the absence of an emulsifier followed by heating under an alkaline condition, and purports that a latex consisting of a carrier particle whose particle size is 0.3 to 0.8 μm can be obtained by increasing the amount of a catalyst based on styrene monomer. On the other hand, Japanese Kokoku Publication Hei-1-36484 discloses a method for producing a diagnostic agent by synthesizing a latex in aqueous solution containing an oxide or hydroxide of a divalent metal.

However, a method employing a latex comprising a carrier particle having a large particle size involves problems that when the analyte present at high concentration, the change of optical density resulting from the carrier particle aggregation exceeds the measurable range to make it impossible to obtain a change of optical density corresponding to the amount of the analyte, that it is likely to reflect a non-specific aggregation reaction and also that the storage over a prolonged period is impossible due to the absence of the stability.

On the other hand, Japanese Kokai Publication Sho-63-65369 discloses a method employing a latex reagent obtained by sensitizing latexes comprising two or more kinds of carrier particles having different average particle sizes with an antibody or antigen and mixing in a certain ratio. This method attempts to achieve a performance having two profiles, namely, a wide range of the assay attributable to the latex comprising a carrier particle having a small particle size and a high sensitivity at a low concentration region attributable to the latex consisting of a carrier particle having a large particle size.

Japanese Kokoku Publication Sho-63-14783 discloses a latex consisting of two kinds of carrier particles having different particle size ranges which are loaded with an identical antigen or antibody in at least two different amounts.

Japanese Patent No. 2588174 discloses a method for assaying an antigen-antibody reaction which comprises reacting a latex obtained by sensitizing two or more kinds of particles having different average particle sizes with an antigen or antibody followed by mixing or a latex obtained by mixing two or more particles having different average particle sizes followed by sensitizing with the antigen or antibody, with an antigen against the sensitizing antibody or an antibody against the sensitizing antigen in water and measuring the change of the absorbance upon irradiation, wherein a carrier particle having an average particle size of 0.05 to 0.3 μm and a carrier particle having an average particle size of 0.3 to 1.0 μm are mixed and wherein a light whose wavelength is at least 2.5 times the average particle size of the mixed particles and is also 0.6 to 2.4 μm are irradiated.

Japanese Kokai Publication Hei-5-18973 discloses an immunological assay method which comprises, depending on the amount of a component to be assayed by an immunological reaction, a carrier particle having a particle size of 0.1 μm or less in which a component reactive with the component to be assayed is insolubilized is combined with at least one of the component reactive with the component to be assayed and a carrier particle having a particle size more than 0.1 μm in which the reactive component is insolubilized, and subjected to the reaction with a sample containing the component to be assayed, as well as a reagent employed in the same.

However, such methods employing the latex consisting of several carrier particles having different average particle sizes are difficult to prepare a latex reagent, and, has a problem that the obtained reagent varies in the performance time by time of the preparation even if an identical operator prepares the reagent in accordance with a certain protocol using the particle having an identical average particle size and an identical CV values.

SUMMARY OF THE INVENTION

An objective of the invention is to provide a carrier particle latex for an assay reagent capable of assaying a biological sample at a wide range of the concentration in an immunoserological test and capable of being stored stably for a prolonged period, as well as an assay reagent employing the same.

The first aspect of the invention is a carrier particle latex for an assay reagent comprising a carrier particle comprising a copolymer of a polymerizable monomer having a phenyl group and a polymerizable monomer having a phenyl group and a sulfonate, wherein said carrier particle has a surface sulfonic acid group amount of 0.005 to 0.7 μmol/m$^2$ and an average particle size of 0.01 to 1.5 μm.

The second aspect of the invention is a carrier particle latex for an assay reagent comprising a carrier particle comprising a copolymer of a polymerizable monomer having a phenyl group and a polymerizable monomer having a phenyl group and a sulfonate, wherein said carrier particle comprises two or more kinds of particles having different surface sulfonic acid group amounts. In the carrier particle latex for an assay reagent according to the second aspect of the invention, it is preferable that the carrier particle has a surface sulfonic acid group amount of 0.005 to 0.7 μmol/m$^2$. In the carrier particle latex for an assay reagent according to the second aspect of the invention, it is preferable that the carrier particle comprises a carrier particle (A) having a surface sulfonic acid group amount of 0.005 μmol/m$^2$ or higher and less than 0.12 μmol/m$^2$ and a carrier particle (B) having a surface sulfonic acid group amount of 0.12 μmol/m$^2$ or higher and 0.7 μmol/m$^2$ or less. In the carrier particle latex for an assay reagent according to the second aspect of the invention, it is preferable that the weight ratio of the carrier particle (A) and the carrier particle (B) contained is represented by (A)/(B)=1/10 to 10/1.

The third aspect of the invention is a carrier particle latex for an assay reagent comprising a carrier particle comprising a copolymer of a polymerizable monomer having a phenyl group and a polymerizable monomer having a phenyl group and a sulfonate, wherein said carrier particle has an average particle size of 0.04 to 0.1 μm and a CV value of the particle size of 8 to 20%. In the carrier particle latex for an assay reagent according to the third aspect of the invention, it is preferable that the carrier particle has a surface sulfonic acid group amount of 0.005 to 0.7 μmol/m$^2$.

It is preferable that the carrier particle latex for an assay reagent according to the first, second or third aspects of the invention contains substantially no emulsifier. Also in the carrier particle latex for an assay reagent according to the first, second or third aspects of the invention, it is preferable that the polymerizable monomer having the phenyl group is styrene and the polymerizable monomer having the phenyl group and a sulfonate is styrene sulfonate.

The fourth aspect of the invention is an assay reagent wherein a substance specifically binding to an analyte is supported on the carrier particle of a carrier particle latex for an assay reagent according to the first, second or third aspects of the invention.

BRIEF DESCRIPTION OF THE DRAWING(S)

DETAILED DISCLOSURE OF THE INVENTION

Figure 1:
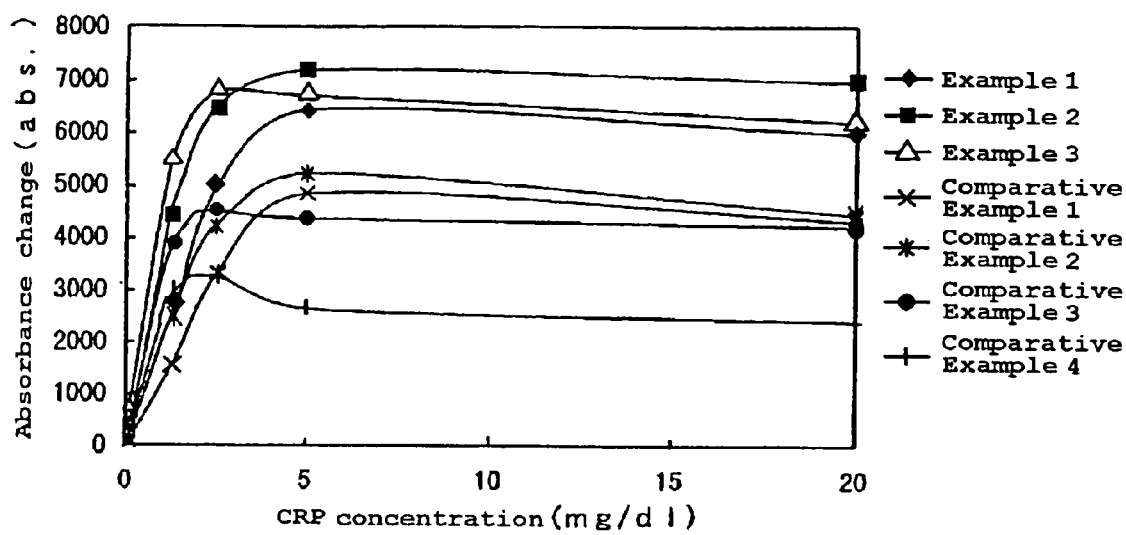
FIG. 1 shows the results of the assay of samples performed immediately after the preparation of the assay reagents prepared in Examples 1 to 3 and Comparative Examples 1 to 4.

The invention is detailed below.

The carrier particle latex for an assay reagent of the first aspect of the invention comprises a carrier particle comprising a copolymer of a polymerizable monomer having a phenyl group and a polymerizable monomer having a phenyl group and a sulfonate.

The polymerizable monomer having a phenyl group described above is not limited particularly, and may include, for example, styrene, divinylbenzene, ethylstyrene, α-methylstyrene, p-methylstyrene, p-chlorostyrene, chloromethylstyrene and the like. They may be used alone or in combination of two or more of them. Among those listed above, styrene is used preferably.

The polymerizable monomer having a phenyl group and a sulfonate described above is not limited particularly as long as it allows a carrier particle surface after polymerization to contain the sulfonate group, and may include, for example, styrenesulfonate, divinylbenzene sulfonate, ethylstyrenesulfonate, α-methylstyrenesulfonate and the like. The salt mentioned here is not limited particularly, and may include, for example, a sodium salt, potassium salt, lithium salt, ammonium salt and the like. They may be used alone or in combination of two or more of them. Among those listed above, a styrenesulfonate is preferred, with sodium styrenesulfonate being more preferred.

The carrier particle described above is obtained by copolymerizing the polymerizable monomer having a phenyl group described above and the polymerizable monomer having a phenyl group and a sulfonate described above. The copolymerization method described above may use any known method, such as a method in which a reaction vessel containing water as a solvent is charged with the polymerizable monomer having a phenyl group described above, the polymerizable monomer having a phenyl group and a sulfonate described above and the polymerization initiator if necessary together with an emulsifier and the reactant is stirred under nitrogen atmosphere. In such a case, the polymerization temperature is preferably 50 to 100° C., more preferably 60 to 85° C. The polymerization time period is usually 5 to 50 hours, although it may vary depending on the conditions of the compositions and concentrations of the polymerizable monomers and, the polymerization initiator.

The polymerization initiator described above is not limited particularly, and may include, for example, a persulfate and the like. The persulfates may include, for example, potassium persulfate, sodium persulfate, ammonium persulfate and the like. An amount of the polymerization initiator is not limited particularly, it is usually 0.01 to 1% by weight based on the polymerizable monomer.

Without using the emulsifier described above is preferable usually since the assay accuracy is affected adversely when the emulsifier is contained in the carrier particle latex for an assay reagent of the first aspect of the invention, it is allowed for example in the case where it is necessary for adjusting the amount of the sulfonate group on the surface of the carrier particle described above. Nevertheless, in view of the removal in a post treatment step after the polymerization, the emulsifier may be used in an amount preferably of 1% by weight or less, more preferably 0.5% by weight or less, still more preferably 0.01 to 0.02% by weight based on the polymerizable monomer having a phenyl group.

The amount of the polymerizable monomer having a phenyl group and a sulfonate described above based on the polymerizable monomer having a phenyl group described above is preferably 2% by weight or less, more preferably 0.0001 to 1.5% by weight, still more preferably 0.001 to 1.2% by weight for the purpose of adjusting the particle surface sulfonic acid group amount within the range from 0.005 to 0.7 $\mu mol/m^2$. By copolymerizing the both components in this ratio, it becomes possible to adjust the carrier particle surface sulfonic acid group amount described above within the range from 0.005 to 0.7 $\mu mol/m^2$.

Depending on the purpose of use of the carrier particle latex for an assay reagent according to the invention, a further polymerizable unsaturated monomer may be added upon the copolymerization. Such a polymerizable unsaturated monomer is not limited particularly as long as it can be used in an ordinary radical polymerization, and may include, for example, (meth)acrylic acid, (meth)acrylate, styrene derivative, (meth)acrylonitrile, (meth)acrylamide, vinyl halide, vinyl ester, (meth)acrolein, maleic acid derivative, fumaric acid derivative and the like. In the present invention, (meth)acrylic acid means acrylic acid or methacrylic acid.

The carrier particle described above has a surface sulfonic acid group amount of 0.005 to 0.7 $\mu mol/m^2$. The inventors of the present invention discovered that a carrier particle surface sulfonic acid group amount within the range specified above leads to a marked improvement in the assay sensitivity and, allows a trace concentration of a protein as an analyte to be assayed over a wide range from a low concentration to a high concentration, whereby establishing the invention. A carrier particle surface sulfonic acid group amount less than 0.005 $\mu mol/m^2$ leads to a liability to a non-specific aggregation, while an amount more than 0.7 $\mu mol/m^2$ leads to a reduced aggregation reactivity, which results in a poor sensitivity. Preferably, the amount is 0.02 to 0.5 $\mu mol/m^2$. The carrier particle surface sulfonic acid group amount described above can be determined by an electric conductivity titration method (Journal of Colloid and Interface Sciences, 49 (3), 425, 1974).

The average particle size of the carrier particle described above is 0.01 to 1.5 μm. A size less than 0.01 μm leads to a too small change of optical density upon aggregation which results in a difficulty in obtaining a sensitivity required for an assay and also a too much time required for a centrifugation upon preparation of a reagent which results in an increased cost of the reagent. A size more than 1.5 μm allows the carrier particle aggregation-induced change of optical density to exceed the measurable limit at a high concentration of an analyte, resulting in a difficulty in obtaining a change of optical density corresponding to the amount of the analyte. While the size of a carrier particle may vary depending on the assay method and device using a carrier particle latex for an assay reagent, it is preferably 0.03 to 0.8 μm, more preferably 0.05 to 0.5 μm.

The coefficient of variation of the particle size (CV value) of the carrier particle described above is preferably 10% or less. A value more than 10% may lead to a poor reproducibility of the lots upon preparation of a reagent, which results in a reduction in the reproducibility of the assay reagent.

More preferably it is 5% or less, particularly 3% or less. The coefficient of variation of the particle size described above can be calculated in accordance with the following equation.

Coefficient of variation of particle size (CV value)= Standard deviation of particle size/average particle size The carrier particle latex for an assay reagent according to the first aspect of the invention can be obtained by suspending the carrier particle described above in water or an aqueous solvent. While the concentration of the carrier particle in the carrier particle latex for an assay reagent according to the first aspect of the invention is not limited particularly, it is preferably 1 to 20% by weight in general. A concentration less than 1% by weight leads to a need of a concentration step upon preparation of a regent, while a concentration more than 20% by weight may lead to an aggregation.

The carrier particle latex for an assay reagent according to the first aspect of the invention preferably contains substantially no emulsifier, since it may cause a disadvantage such as an adverse effect on the assay accuracy. The term "substantially" as used herein means that the presence of an emulsifier only in a trace amount after the step for removing the emulsifier is acceptable when the emulsifier is employed in the production of a carrier particle.

The carrier particle latex for an assay reagent according to the first aspect of the invention has a carrier particle surface sulfonic acid group amount within the range specified above, which leads to a marked improvement in the assay sensitivity and, allows a trace concentration of a protein as an analyte to be assayed over a wide range from a low concentration to a high concentration. Also since it is excellent in terms of the stability for a prolonged period, it is best suited especially to an optical measurement device. Moreover, it is not necessary to add a saccharide and the like to increase the specific gravity of the fluid conducted conventionally for the purpose of avoiding any sedimentation.

The second aspect of the invention is a carrier particle latex for an assay reagent comprising a carrier particle comprising a copolymer of a polymerizable monomer having a phenyl group and a polymerizable monomer having a phenyl group and a sulfonate, wherein said carrier particle comprises two or more kinds of particles having different surface sulfonic acid group amounts and substantially no emulsifier is contained.

The polymerizable monomer having a phenyl group and the polymerizable monomer having a phenyl group and a sulfonate described above are similar to those in the first aspect of the invention.

In the carrier particle latex for an assay reagent according to the second aspect of the invention, a carrier particle comprising two or more kinds of particles having different surface sulfonic acid group amounts is employed. By employing the carrier particle comprising two or more kinds of particles having different surface sulfonic acid group amounts, the resultant carrier particle latex for an assay reagent enables the assay of an antigen-antibody reaction at a high sensitivity and at a high accuracy over a wide range from a low concentration to a high concentration, and thus is suitable for obtaining a reagent which is excellent also in terms of the stability over a prolonged period, especially a reagent suitable for an optical measurement device such as a spectrophotometer, turbidimeter, light scattering photometer and the like.

The carrier particle surface sulfonic acid group amount of the carrier particle latex for an assay reagent according to the second aspect of the invention is preferably 0.005 to 0.7 $\mu mol/m^2$. An amount less than 0.005 $\mu mol/m^2$ leads to a liability to a non-specific aggregation, while an amount more than 0.7 $\mu mol/m^2$ leads to a reduced aggregation and, results in a poor sensitivity. Preferably, the amount is 0.02 to 0.5 $\mu mol/m^2$.

It is preferable that the carrier particle of the carrier particle latex for an assay reagent according to the second aspect of the invention comprises a carrier particle (A) having a surface sulfonic acid group amount of 0.005 $\mu mol/m^2$ or higher and less than 0.12 $\mu mol/m^2$ and a carrier particle (B) having a surface sulfonic acid group amount of 0.12 $\mu mol/m^2$ or higher and 0.7 $\mu mol/m^2$ or less. By employing such a mixture of the carrier particle (A) and the carrier particle (B), the resultant carrier particle latex for an assay reagent enables the assay of an antigen-antibody reaction at a high sensitivity and at a high accuracy over a wide range from a low concentration to a high concentration, and gives a further improvement in the stability over a prolonged period.

A surface sulfonic acid group amount of a carrier particle (A) described above less than 0.005 $\mu mol/m^2$ may result in a carrier particle latex for an assay reagent or an assay reagent as a final product which has a reduced stability over a prolonged period, and may allow the assay reagent to undergo a non-specific aggregation easily, while an amount of 0.12 $\mu mol/m^2$ or higher may lead to a difficulty in the determination at a low concentration. A surface sulfonic acid group amount of a carrier particle (B) described above less than 0.12 $\mu mol/m^2$ may lead to a difficulty in the determination at a high concentration, while an amount more than 0.7 $\mu mol/m^2$ may result in a reduced immunoserological aggregation of the reagent as a final product which leads to an insufficient sensitivity or accuracy of the assay.

The weight ratio of a carrier particle (A) and a carrier particle (B) described above is preferably 1/10 to 10/1 by weight. Departing from this range, a carrier particle latex for an assay reagent suitable for obtaining an assay reagent imparted with the combination of the excellent properties described above may not be obtained.

Preferably, the average particle size of a carrier particle employed in the carrier particle latex for an assay reagent according to the second aspect of the invention is 0.01 to 1.5 $\mu m$. A size less than 0.01 $\mu m$ may lead to a too small change of optical density upon aggregation and results in a difficulty in obtaining a sensitivity required for an assay and, also a too much time required for a centrifugation upon preparation of a reagent and results in an increased cost of the reagent. A size more than 1.5 $\mu m$ allows the aggregation-induced change of optical density to exceed the measurable limit in the presence of a high concentration of an analyte and, results in a difficulty in obtaining a change of optical density corresponding to the amount of the analyte at a high concentration. The size is preferably 0.03 to 0.8 $\mu m$, particularly 0.05 to 0.5 $\mu m$. The coefficient of variation (CV value) of the particle size of a carrier particle employed in the carrier particle latex for an assay reagent according to the second aspect of the invention is preferably 10% or less. A value more than 10% may lead to a poor reproducibility of the lots upon preparation of a reagent and, results in a reduction of the reproducibility of the reagent. More preferably it is 5% or less, particularly 3% or less. The average particle size of the carrier particle (A) may be or may not be similar to that of the carrier particle (B).

A method for producing a carrier particle employed in the carrier particle latex for an assay reagent according to the second aspect of the invention and a method for producing the carrier particle latex for an assay reagent according to the second aspect of the invention are similar to those in the case of the carrier particle latex for an assay reagent according to the first aspect of the invention.

By employing two or more particles whose surface sulfonic acid group amounts are different, the carrier particle latex for an assay reagent according to the second aspect of the invention enables, an assay of an antigen-antibody reaction at a high sensitivity and at a high accuracy over a wide range from a low concentration to a high concentration, and thus is suitable for obtaining a reagent which is excellent also in terms of the stability over a prolonged period, especially a reagent suitable for an optical measurement device such as a spectrophotometer, turbidimeter, light scattering photometer and the like.

The third aspect of the invention is a carrier particle latex for an assay reagent comprising a carrier particle comprising a copolymer of a polymerizable monomer having a phenyl group and a polymerizable monomer having a phenyl group and a sulfonate, wherein said carrier particle has an average particle size of 0.04 to 0.1 µm and a CV value of the particle size of 8 to 20% and wherein substantially no emulsifier is contained.

The polymerizable monomer having a phenyl group and the polymerizable monomer having a phenyl group and a sulfonate described above are similar to those in the first aspect of the invention.

The carrier particle employed in the carrier particle latex for an assay reagent according to the third aspect of the invention has an average particle size of 0.04 to 0.1 µm and a CV value of the particle size of 8 to 20%. By employing such a carrier particle having an average particle size and a CV value of the particle size controlled within a certain range, the resultant product enables the assay of an antigen-antibody reaction over a wide range of the concentration, is excellent also in terms of the stability over a prolonged period and also is suitable for obtaining a reagent for an immunoserological test capable of being applied especially to an optical measurement device. An average particle size less than 0.4 µm leads to a prolonged period required for preparing the reagent, while a size more than 0.1 µm leads to an increased background, which results in a reduced accuracy of the assay at a low concentration. Preferably, the size is 0.05 to 0.095 µm. On the other hand, a CV value of the particle size less than 8% makes the assay impossible over a wide range from a low concentration to a high concentration, while a value more than 20% leads to a difficulty in recovering the particle after centrifugation and upon preparation of the reagent. Preferably the value is 10 to 16%.

The surface sulfonic acid group amount of the carrier particle employed in the carrier particle latex for an assay reagent according to the third aspect of the invention is preferably 0.005 to 0.7 µmol/m$^2$. An amount less than 0.005 µmol/m$^2$ leads to a liability to a non-specific aggregation, while an amount more than 0.7 µmol/m$^2$ leads to a reduced aggregation which results in a poor sensitivity. Preferably, the amount is 0.02 to 0.5 µmol/m$^2$.

A method for producing a carrier particle employed in the carrier particle latex for an assay reagent according to the third aspect of the invention and a method for producing the carrier particle latex for an assay reagent according to the third aspect of the invention are similar to those in the case of the carrier particle latex for an assay reagent according to the first aspect of the invention.

By employing a carrier particle having an average particle size and a CV value of the particle size controlled within a certain range, the carrier particle latex for an assay reagent according to the third aspect of the invention becomes a product which enables the assay of an antigen-antibody reaction over a wide range of the concentration, and is excellent also in terms of the stability over a prolonged period and is suitable for obtaining a reagent for an immunoserological test capable of being applied especially to an optical measurement device.

The fourth aspect of the invention is an assay reagent, wherein a substance specifically binding to an analyte is supported on the carrier particle of a carrier particle latex for an assay reagent according to the first, second and third aspects of the invention.

A substance described above specifically binding to an analyte is not limited particularly as long as it is a immunoserological test reagent (employed in immunological aggregation and aggregation-inhibition reactions) or a bioactive substance employed ordinarily in a biochemical assay, and is preferably one utilizable in an antigen-antibody reaction.

One utilizable in the antigen-antibody reaction described above may include, for example, the antigen or antibody of protein, nucleic acid, nuclear protein, estrogen lipid and the like. The antigen may include, for example, any of various antigen, receptors, enzymes and the like, and β2 microglobulin, C-reactive protein (CRP), human fibrinogen, ferritin, rheumatoid factor (RA), α-fetoprotein (AFP), mycoplasma antigen, HBs antigen and the like. The antibody may include, for example, any of various antibodies against various toxins and pathogenic bacteria, and anti-streptolysin O antibody, anti-estrogen antibody, β2 microglobulin antibody, treponema pallidum antibody, antibody against treponema pallidum lipid antigen, HBs antibody, HBc antibody, HBe antibody and the like. The antibody may also be a fragment such as $F(ab')_2$ in addition to an immunoglobulin molecule itself.

A method for allowing a substance specifically binding to an analyte to be supported on the carrier particle described above is not limited particularly, and a physical and/or chemical bond-mediated supporting mode may be employed in a known method.

The amount of a substance which specifically binds to an analyte and which is supported on the carrier particle described above may vary depending on the type of the substance to be used which specifically binds to an analyte, and is not limited particularly.

The assay reagent according to the fourth aspect of the invention may contain various sensitizers for improving the assay sensitivity and promoting an antigen-antibody reaction. Such a sensitizer may include, for example, an alkylation polysaccharide such as methyl cellulose and ethyl cellulose as described in Japanese Kokai Publication Hei-2-173567 as well as pullulan and polyvinyl pyrrolidone as described in Japanese Kokai Publication Hei-5-180838 and the like.

The assay reagent according to the fourth aspect of the invention may contain proteins or degradation products thereof such as albumin (bovine serum albumin, ovalbumin), casein, gelatin and the like, amino acids or surfactant, for the purpose of suppressing the non-specific aggregation caused by other substances in a sample or for the purpose of increasing the stability of a reagent.

The assay reagent according to the fourth aspect of the invention may be used after being diluted with a suitable diluent. Such a diluent may be used any buffer solution at pH 5.0 to 9.0, such as a phosphate buffer, glycine buffer, tris buffer, borate buffer, citrate buffer and the like.

Using an assay reagent according to the fourth aspect of the invention, the reaction amount of an analyte in a sample can be assayed by means of an optical measurement of the degree of the aggregation of a carrier particle resulting from the reaction between the analyte in the sample and a substance which specifically binds to an analyte and which is supported on the carrier particle. Such an optical measurement may employ any optical device capable of detecting the scattering light intensity, transmission intensity, absorbance and the like, especially an ordinary automatic biochemical analyzer.

A method for optically measuring the degree of the aggregation may be any known method, such as a turbidimetric method in which the formation of the aggregation is monitored as an increase in the turbidity, a method in which the formation of the aggregation is monitored as a change in the particle size distribution or average particle size, a turbidimetic method with integrating sphere in which the change in the forward scattering light as a result of the formation of the aggregation is assayed using an integration sphere to compare the ratio with the transmission intensity. The method for assaying also exemplified is a rate assay in which the aggregation degree is determined based on the increment in the measured value (increasing rate) between at least two measured values obtained at different time points; and an end-point assay in which the aggregation degree is determined based on a single measured value at a certain time point (usually the time point assumed to be the end-point of the reaction). Among those listed above, a turbidimetric method is preferred since the assay can conveniently and rapidly be performed.

BEST MODE FOR CARRYING OUT THE INVENTION

The invention is further detailed in the following Examples, which are not intended to restrict the invention.

EXAMPLE 1

[Preparation of Carrier Particle]

A glass reaction vessel (2 L) fitted with a stirrer, reflux condenser, thermometer, nitrogen inlet and jacket was charged with 1500 g of distilled water, 280 g of styrene, 0.9 g of sodium styrenesulfonate and aqueous solution of 0.5 g of potassium persulfate dissolved in 10 g of distilled water, and purged with nitrogen gas, and then, the polymerization was performed at 70° C. with stirring for 24 hours.

After completion of the polymerization, the solution was filtered through a paper filter to obtain a carrier particle. The particle size and the surface sulfonic acid group amount of the resultant carrier particle were assayed by the methods described below. The results are shown in Table 1.

(Method for Measuring Carrier Particle Size)

A photograph of a carrier particle was taken using a transmission electron microscope, and subjected to an image analysis to determine the particle size.

(Method for Assaying Carrier Particle Surface Sulfonic Acid Group Amount)

The carrier particle was dialyzed against a purified water for 48 hours using a cellophane tube dialysis membrane, and any remaining monomers were removed. 10 g of these particles on the dried basis was weighed into a 4-neck glass vessel, diluted to 150 ml with distilled water, and stirred using a stirrer tip. The resultant solution was designated as Solution A.

Then, N/100-sodium hydroxide (manufactured by WAKO PURE CHEMICAL INDUSTRIES, LTD) was placed in an electric burette model ATB-310 appended to a potentiometric conductivity titration processor (model AT-310, manufactured by KYOTO ELECTRONICS MANUFACTURING CO., LTD), and a conductivity electrode was immersed in Solution A, and a nitrogen inlet, an exhaust tube and a pH electrode were placed. Then the N/100-sodium hydroxide was dropped (dropping rate of 0.05 ml/150 to 500 seconds: adjusted based on the sulfonic acid amount to be assayed), and the equivalent point was determined based on the change in the conductivity using the potential conductivity titration processor (model AT-310), whereby calculating the intended sulfonic acid amount.

[Preparation of Assay Reagent]

250 μl of aqueous solution which was adjusted at 5% (w/v) by employing the resultant carrier particle was placed in a 8 ml glass tube. To this, 550 μl of anti-human CRP goat serum (produced by DAKO, protein concentration: 12 mg/mL) was added at once, and allowed to be adsorbed with stirring gently for 1 hour at 37° C. Then, 450 μl of glycine buffer (pH8.5) containing 1.0% by weight of a bovine serum albumin (hereinafter sometimes referred to as BSA) was added at once, and the blocking treatment was effected with stirring for 1 hour at 37° C.

An aliquot of the suspension after the blocking treatment was placed in a 8 ml centrifugating tube, centrifuged at 15000 rpm at 4° C. for 30 minutes, removed the supernatant, and residue was redispersed in the glycine buffer (pH8.5) containing 1.0% by weight of BSA, and subjected twice to an excessive antibody treatment.

The particle which had subjected to the excessive antibody treatment was combined with 2.5 ml of the glycine buffer (pH8.5) containing 1.0% by weight of BSA, after ultrasonication, combined further with the glycine buffer (pH8.5) containing 1.0% by weight of BSA, adjusted to the final volume of 30 ml, whereby preparing an assay reagent.

[Evaluation of Assay Reagent Performance]

1) Evaluation of Assay Sensitivity

Using the resultant assay reagent, the change of the absorbance upon measurement of a sample was determined. In the determination, 132 μl of the assay reagent was used for each sample measurement, together with 132 μl of the glycine buffer (pH8.5) containing 1.0% by of BSA as a diluent of sample and 2 μl of the sample having a CRP concentration of 0.08 to 20 mg/dl, whereby determining the change in the absorbance of each sample. As a measurement device, an automatic biochemical analyzer (manufactured by HITACHI LTD, model 7170 automatic analyzer) was employed under the condition involving the detection wavelength of 800 nm and the light observation points of 2 point-end 21-34p. The results are shown in FIG. 1.

As evident from FIG. 1, the assay reagent obtained here enabled a highly sensitive assay of the sample over the range from a low concentration to a high concentration.

2) Evaluation of Reagent Stability

The resultant assay reagent was stored for 6 months at 4° C. and then examined for the assay sensitivity using a sample whose CRP concentration was 0.08 to 20 mg/dl in the same manner as the method described above.

Figure 2:
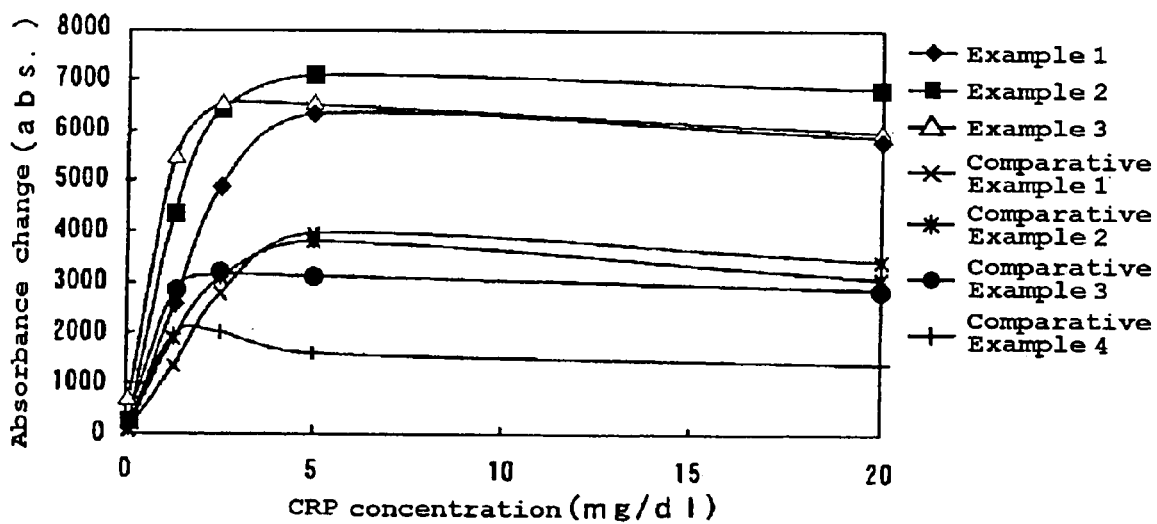
FIG. 2 shows the results of the assay of samples performed after the stability test of the assay reagents prepared in Examples 1 to 3 and Comparative Examples 1 to 4.

The results are shown in FIG. 2.

As evident from FIG. 2, similarly to the assay reagent immediately after preparation, the assay reagent even after storage for a prolonged period enabled a highly sensitive assay of the sample over the range from a low concentration to a high concentration, and was proven to be able to keep the performance stably over a prolonged period.

EXAMPLES 2 TO 3, COMPARATIVE EXAMPLES 1 TO 4

Except for charging the distilled water, styrene and sodium styrenesulfonate as indicated in Table 1, a carrier particle was produced in the same manner as Example 1.

The particle size and the surface sulfonic acid group amount of the resultant carrier particle were measured in the same manner as Example 1 and the results are shown in Table 1.

Then, BSA-containing glycine buffer (pH8.5) was prepared at the sensitization amount per surface area similar to that in Example 1, and assay reagents for each of Examples and Comparative Examples were prepared.

The resultant regents were examined for their assay sensitivities in the same manner as Example 1. The results are shown in FIG. 1.

As evident from FIG. 1, the assay reagents prepared in Examples 2 and 3 exhibited satisfactory results similarly to Example 1. On the contrary, the assay reagents prepared in Comparative Examples 1 to 4 exhibited low sensitivities.

Then the reagents prepared here were stored for 6 months at 4° C., and examined for the stability of the reagents in the same manner as Example 1. The results are shown in FIG. 2.

As evident from FIG. 2, any of the reagents prepared in Examples 2 and 3 enabled, even after the storage for a prolonged period, a highly sensitive assay of the sample over the range from a low concentration to a high concentration similar to that exhibited immediately before preparation in the same manner as Example 1, thus revealing that it can kept its performance stably for a prolonged period. On the contrary, any of the reagent prepared in Comparative Examples 1 to 4 exhibited, after the storage for a prolonged period, a sensitivity which was lower when compared to that observed immediately after preparation, reflecting a deteriorated reagent performance.

TABLE 1

|  | Example1 | Example2 | Example3 | Comparative Example1 | Comparative Example2 | Comparative Example3 | Comparative Example4 |
| --- | --- | --- | --- | --- | --- | --- | --- |
| Composition (g) |  |  |  |  |  |  |  |
| Distilled water | 1500 | 1500 | 1500 | 1500 | 1500 | 1500 | 1500 |
| Styrene | 280 | 250 | 250 | 280 | 250 | 250 | 250 |
| Sodiumstyrene sulfonate | 0.9 | 3.0 | 2.0 | 5.5 | 5.5 | 4.7 | 0.4 |
| Average particle size (μm) | 0.151 | 0.217 | 0.405 | 0.153 | 0.222 | 0.401 | 0.400 |
| Surface sulfonic acid group amount (μmol/m$^2$) | 0.02 | 0.30 | 0.15 | 0.84 | 0.95 | 0.90 | 0.003 |

EXAMPLE 4, COMPARATIVE EXAMPLE 5

BSA-containing glycine buffer (pH8.5) was prepared so that the antibody sensitization amounts per surface area of the carrier particles produced in Example 3 and Comparative Example 3 became 80% based on those of Example 3 and Comparative Example 3 respectively, and used to prepare assay reagents, which were designated as Example 4 and Comparative Example 5, respectively.

Figure 3:
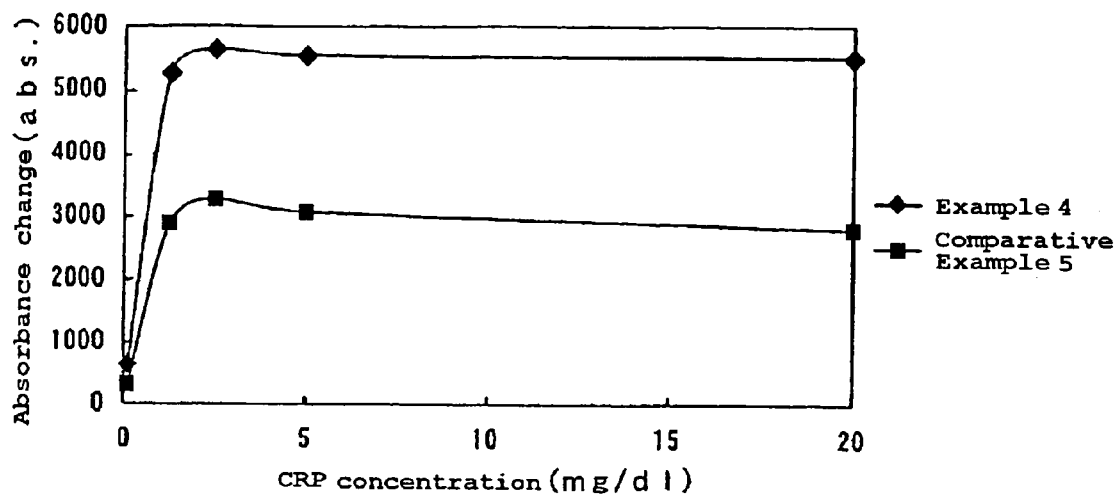
FIG. 3 shows the results of the assay of samples performed immediately after the preparation of the assay reagents prepared in Example 4 and Comparative Example 5.

The resultant assay reagents were examined for the sensitivity in the same manner as Example 1, and the results are shown in FIG. 3.

As evident from FIG. 3, the assay reagent prepared in Example 4 exhibited satisfactory results similarly to Example 1. On the contrary, the assay reagent prepared in Comparative Example 5 exhibited low sensitivities.

Then the reagents prepared here were stored for 6 months at 4° C., and examined for the stability of the reagents in the same manner as Example 1. The results are shown in FIG. 4.

Figure 4:
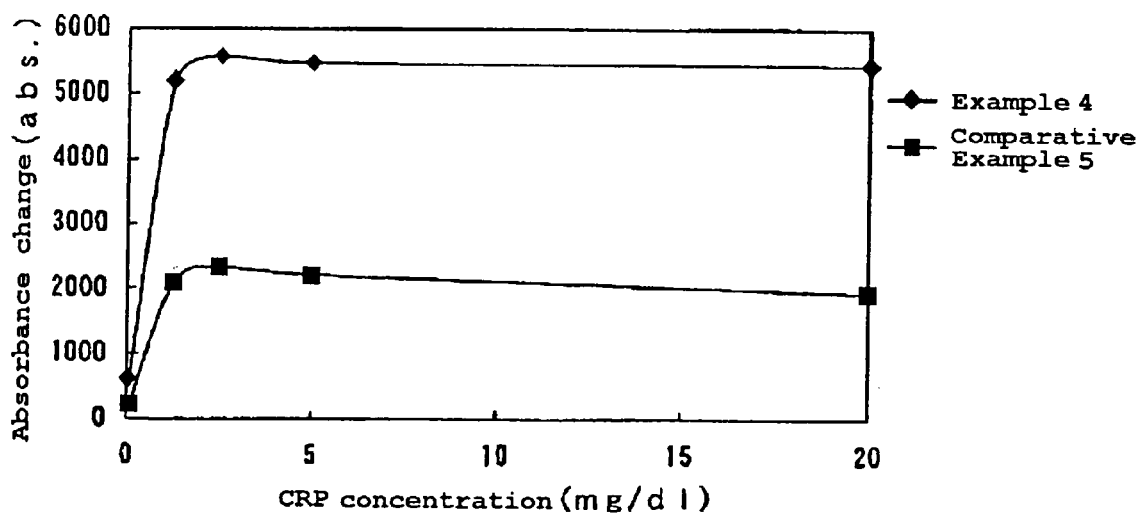
FIG. 4 shows the results of the assay of samples performed after the stability test of the assay reagents prepared in Example 4 and Comparative Example 5.

As evident from FIG. 4, the reagent prepared in Example 4 enabled, a highly sensitive assay of the sample over the range from a low concentration to a high concentration similar to that exhibited immediately before preparation, thus revealing that it can kept its performance stably for a prolonged period. On the contrary, the reagent prepared in Comparative Example 5 exhibited, after the storage for a prolonged period, a sensitivity which was lower when compared to that observed immediately after preparation, reflecting a deteriorated reagent performance.

EXAMPLES 5 TO 7, COMPARATIVE EXAMPLES 6 TO 8

[Preparation of Carrier Particle]

A glass reaction vessel (2 L) fitted with a stirrer, cooling coil, thermometer, jacket and the like was charged with the starting material whose composition is shown in Table 2, purged with nitrogen, and subjected to a copolymerization for 48 hours with controlling the reaction temperature from 70° C. to 71° C. with stirring. As a catalyst for polymerization, aqueous solution of 0.5 g of potassium persulfate dissolved in 10 g of distilled water was employed. A nonionic emulsifier (EMULGEN 804S, manufactured by Kao Corporation) was employed in Examples 5 and 6 and Comparative Example 6, and an anionic emulsifier (NEOPELEX F-25, manufactured by Kao Corporation) was employed in Example 7 and Comparative Example 7.

The resultant carrier particles were taken out and examined for their particle sizes and the surface sulfonic acid group amounts similarly to Example 1.

The results are shown in Table 2.

[Preparation of Assay Reagent]

250 µl of aqueous solution which was adjusted at 5% by employing the carrier particle obtained in Example 5 was placed in a 8 ml glass tube, to which then 550 µl of anti-human CRP goat serum (produced by DAKO, protein concentration: 12 mg/mL, also referred to as an antibody solution) was added, and allowed to be adsorbed with stirring for 1 hour at 37° C., and then combined with 450 µl of BSA (bovine serum albumin)-containing glycine buffer (pH8.5), and the blocking treatment was effected with stirring for 60 minutes at 37° C.

An aliquot of the suspension after the blocking treatment was placed in a 8 ml centrifugating tube, centrifuged at 15000 rpm for 50 minutes, removed the supernatant, redispersed in the BSA-containing glycine buffer (pH8.5), subjected twice to an excessive antibody treatment, combined with 2.5 ml of the BSA-containing glycine buffer (pH8.5), after ultrasonication, and then combined further with the BSA-containing glycine buffer (pH8.5) to make the final volume 30 ml, whereby preparing the assay reagent.

Except for preparing BSA-containing glycine buffer (pH8.5) so that the antibody sensitization amounts per surface area of the carrier particles produced in Examples 6 and 7 and Comparative Examples 6 to 8 became similar, the assay reagents were prepared in the same manner as Example 5.

The centrifugation was conducted at 15000 rpm for 50 minutes in Example 5 and Comparative Example 6, at 15000 rpm for 45 minutes in Example 6 and Comparative Example 7 and at 15000 rpm for 38 minutes in Example 7 and Comparative Example 8.

[Evaluation of Assay Reagent Performance]

Using each of the resultant assay reagents, the change in the absorbance observed upon measuring samples whose CRP concentration ranging from 0.08 to 20 mg/dl were determined under the conditions specified below.

Figure 5:
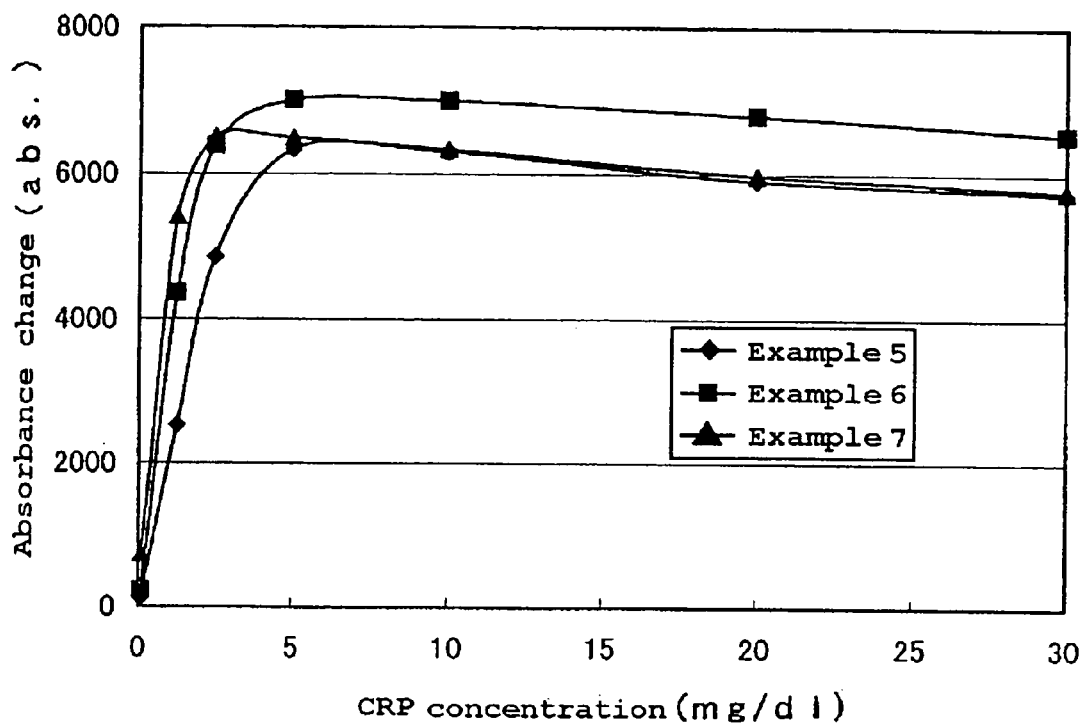
FIG. 5 shows the results of the assay of samples using the reagents prepared in Examples 5 to 7.
Figure 6:
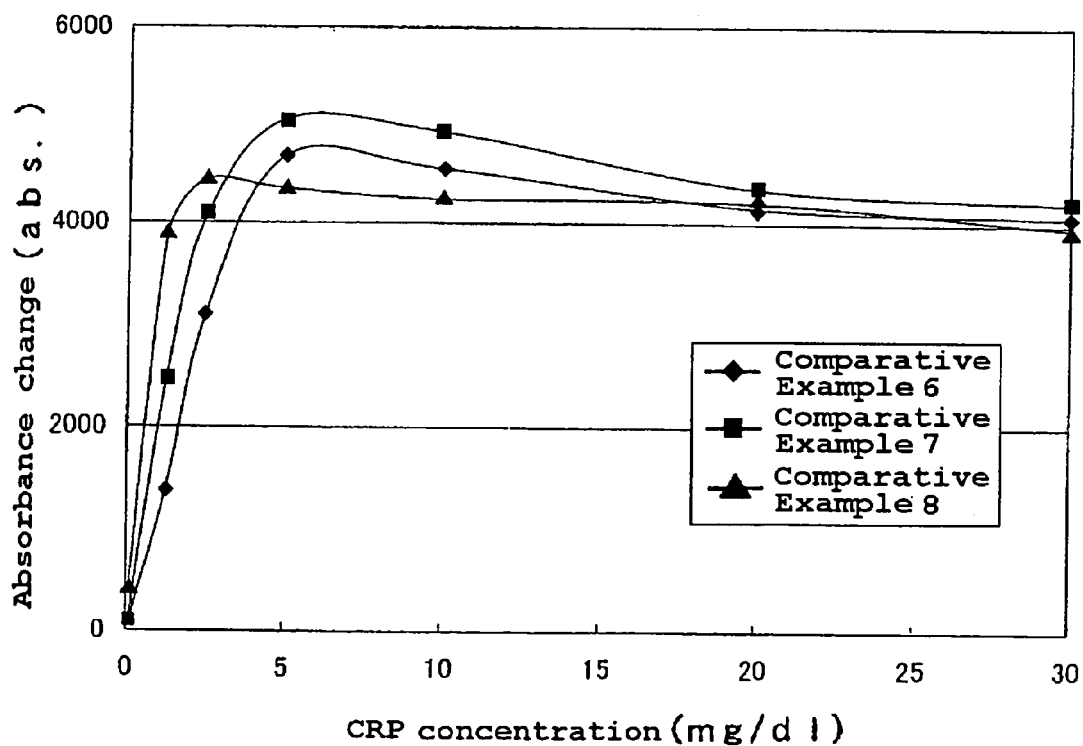
FIG. 6 shows the results of the assay of samples using the reagents prepared in Comparative Examples 6 to 8.

The results are shown in FIG. 5 and FIG. 6.

Instrument: manufactured by HITACHI LTD, model 7170 automatic analyzer
Volumes: Sample: 2 µL
Diluent (R1): 132 µL (Composition of diluent: 1% by weight BSA-containing glycine buffer)
Assay reagent: 132 µL
Detection wavelength: 800 nm
Light observation point: 2 point-end 21-34p

TABLE 2

|  | Example5 | Example6 | Example7 | Comparative Example6 | Comparative Example7 | Comparative Example8 |
|---|---|---|---|---|---|---|
| Composition (g) | | | | | | |
| Distilled water | 1500 | 1500 | 1500 | 1500 | 1500 | 1500 |
| Styrene | 280 | 250 | 250 | 280 | 250 | 250 |
| Sodium styrene sulfonate | 0.9 | 3.0 | 2.0 | 0.9 | 5.5 | 4.7 |
| Emulsifier | 0.05 | 0.03 | 0.027 | 2.9 | 2.6 | 0 |
| Average particle size (µm) | 0.147 | 0.212 | 0.400 | 0.149 | 0.217 | 0.401 |
| Surface sulfonic acid group amount (µmol/m$^2$) | 0.019 | 0.27 | 0.144 | 0.87 | 0.92 | 0.90 |

[Preparation of Carrier Particle]

A glass reaction vessel (2 L) fitted with a stirrer, cooling coil, thermometer, jacket and the like was charged with certain amounts of distilled water, styrene and sodium styrenesulfonate shown in Table 3, further charged with aqueous solution of 0.5 g of potassium persulfate (initiator) dissolved in 10 g of distilled water, purged with nitrogen, subjected to a copolymerization for 48 hours with controlling the reaction temperature at 71° C. to 73° C. with stirring, whereby obtaining 6 types of the carrier particles, namely, (a) to (f). The particle size and the surface sulfonate group amount of each resultant carrier particle were measured in the same manner as Example 1. The results are shown in Table 3.

TABLE 3

| | Carrier particle | | | | | |
|---|---|---|---|---|---|---|
| | (a) | (b) | (c) | (d) | (e) | (f) |
| Composition (g) | | | | | | |
| Distilled water | 1500 | 1500 | 1500 | 1600 | 1500 | 1500 |
| Styrene | 280 | 280 | 250 | 280 | 280 | 250 |
| Sodium styrene sulfonate | 0.9 | 2.5 | 2.0 | 3.5 | 5.5 | 4.7 |
| Average particle size (μm) | 0.151 | 0.153 | 0.405 | 0.409 | 0.153 | 0.401 |
| Surface sulfonic acid group amount (μmol/m$^2$) | 0.02 | 0.59 | 0.15 | 0.30 | 0.84 | 0.90 |

EXAMPLE 8

[Preparation of Assay Reagent]

The carrier particle whose solid weight ratio between the carrier particle (a) and the carrier particle (b) was adjusted to (a)/(b)=1/10 was employed, and combined with distilled water to adjust the % solid at 10% by weight, and 250 ml of an aliquot was placed in a 8 ml glass tube, to which then 170 μl of anti-human CRP goat serum (protein concentration: 18 mg/mL, produced by DAKO, also referred to as an antibody solution) was added, and allowed to be adsorbed with stirring for 1 hour at 37° C., and then combined with 2080 μl of BSA (bovine serum albumin)-containing glycine buffer (pH8.5), and the blocking treatment was effected with stirring for 60 minutes at 37° C. An aliquot after the blocking treatment was placed in a 8 ml centrifugating tube, centrifuged at 15000 rpm for 50 minutes, removed the supernatant, redispersed in the BSA-containing glycine buffer (pH8.5), and subjected twice to an excessive antibody treatment, and then combined with 2.5 ml of the BSA-containing glycine buffer (pH8.5), after ultrasonication, combined further with the BSA-containing glycine buffer (pH8.5), adjusted to the final volume of 5 ml, whereby preparing an assay reagent.

[Evaluation of Assay Reagent Performance]

Using each of the resultant assay reagents, the change in the absorbance observed upon measuring samples whose CRP concentration ranging from 0.08 to 20 mg/dl were determined under the conditions specified below.

Figure 7:
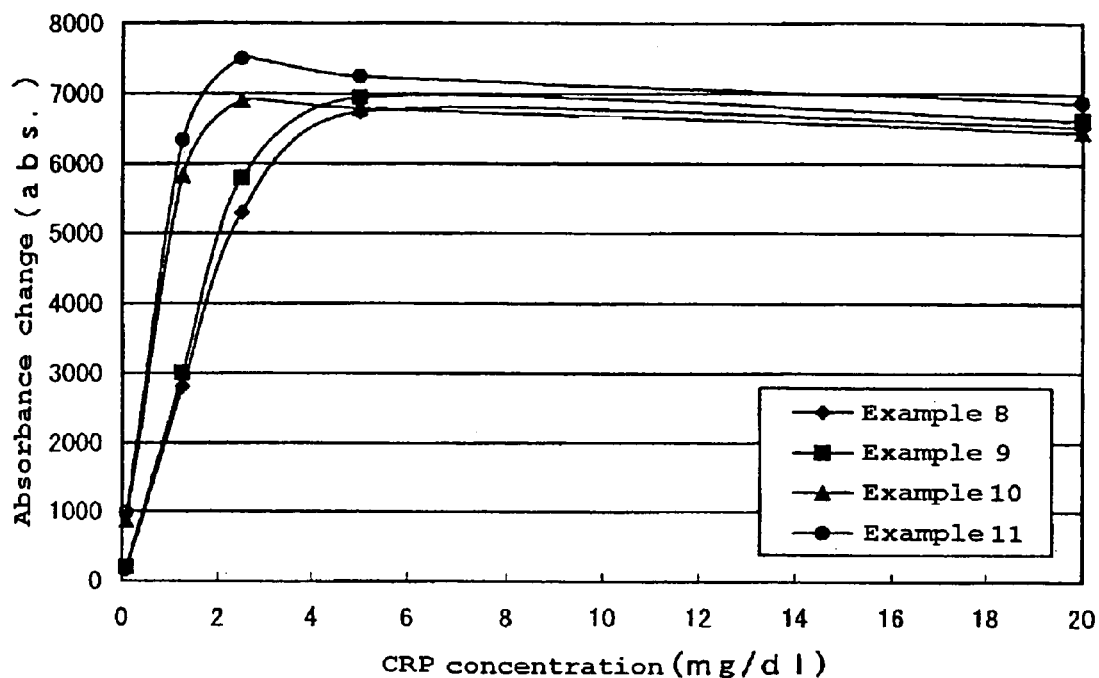
FIG. 7 shows the results of the assay of samples using the reagents prepared in Examples 8 to 11.

The results are shown in FIG. 7.

Instrument: manufactured by HITACHI LTD, model 7150 automatic analyzer
Volumes:Sample: 3 μL
  Diluent (R1): 270 μL (Composition of diluent: 1% by weight BSA-containing glycine buffer)
Assay reagent: 90 μL
Detection wavelength: 800 nm
Light observation point: 2 point-30-50p

EXAMPLE 9

An assay reagent was prepared in the same manner as Example 8 except for using the carrier particle whose solid weight ratio between the carrier particle (a) and the carrier particle (b) was adjusted to (a)/(b)=10/1.

EXAMPLE 10

An assay reagent was prepared in the same manner as Example 8 except for using the carrier particle whose solid weight ratio between the carrier particle (c) and the carrier particle (d) was adjusted to (c)/(d)=1/10.

EXAMPLE 11

An assay reagent was prepared in the same manner as Example 8 except for using the carrier particle whose solid weight ratio between the carrier particle (c) and the carrier particle (d) was adjusted to (c)/(d)=10/1.

Each of the assay reagents obtained in Examples 9 to 11 was examined for its performance (sensitivity) in the same manner as Example 8. The results are shown in FIG. 7.

COMPARATIVE EXAMPLE 9

An assay reagent was prepared in the same manner as Example 8 except for using the carrier particle (a) alone as a carrier particle and preparing BSA-containing glycine buffer (pH8.5) so that the antibody sensitization amounts per surface area of the carrier particle became similar to that in Example 8.

COMPARATIVE EXAMPLE 10

An assay reagent was prepared in the same manner as Example 8 except for using the carrier particle (d) alone as a carrier particle and preparing BSA-containing glycine buffer (pH8.5) so that the antibody sensitization amounts per surface area of the carrier particle became similar to that in Example 8 and also performing the centrifugation at 15000 rpm for 38 minutes.

COMPARATIVE EXAMPLE 11

An assay reagent was prepared in the same manner as Example 8 except for using the carrier particle (e) alone as a carrier particle and preparing BSA-containing glycine buffer (pH8.5) so that the antibody sensitization amounts per surface area of the carrier particle became similar to that in Example 8.

COMPARATIVE EXAMPLE 12

An assay reagent was prepared in the same manner as Example 8 except for using the carrier particle (f) alone as a carrier particle and preparing BSA-containing glycine buffer (pH8.5) so that the antibody sensitization amounts per surface area of the carrier particle became similar to that in Example 8 and also performing the centrifugation at 15000 rpm for 38 minutes.

Each of the assay reagents obtained in Comparative Examples 9 to 12 was examined for its performance (sensitivity) in the same manner as Example 8. The results are shown in FIG. 8.

As evident from FIG. 7, any of the assay reagents prepared in Examples 8 to 11 caused a substantial change in the absorbance over a wide range of the concentration of the CRP from 0.08 to 20 mg/dl, exhibiting an excellent sensitivity.

Figure 8:
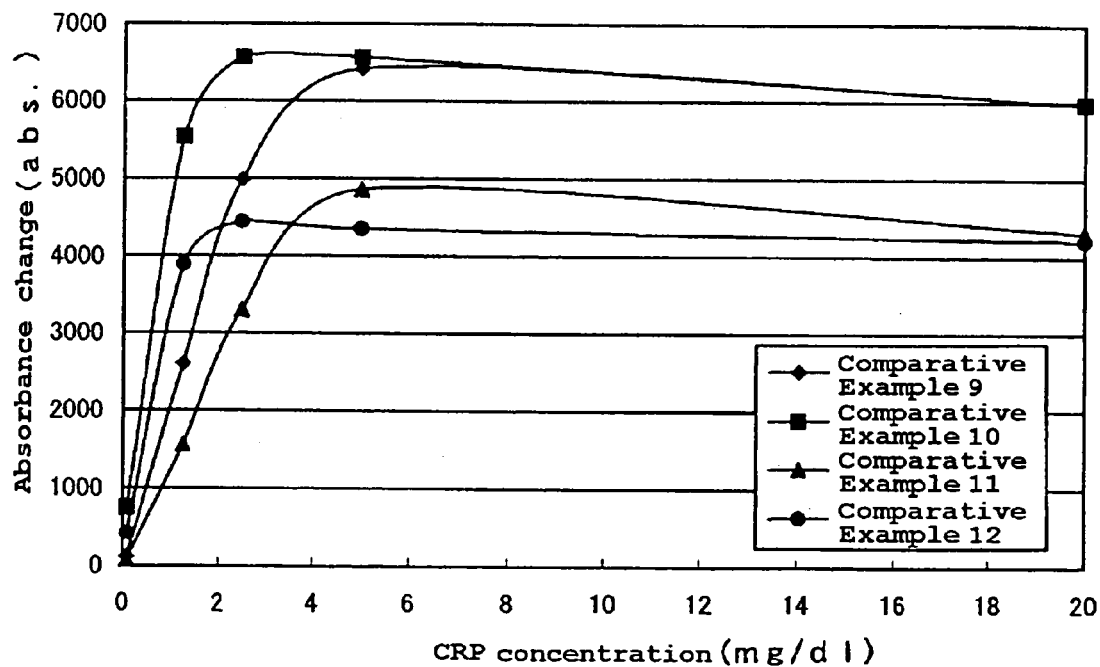
FIG. 8 shows the results of the assay of samples using the reagents prepared in Comparative Examples 9 to 12.

On the contrary, as evident from FIG. 8, any of the reagents of Comparative Examples 9, 11 and 12 employing each as a sole carrier particle, the carrier particles (a), (e) and (f), respectively, caused a small change in the absorbance over a wide range of the concentration of the CRP from 0.08 to 20 mg/dl, exhibiting a poor sensitivity. The reagent of Comparative Example 10 employing as a sole carrier particle the carrier particles (d) caused a small change of the absorbance at a high concentration of the CRP from 5 to 20 mg/dl, exhibiting a poor sensitivity at the high concentration.

[Preparation of Carrier Particle]

A glass reaction vessel (2 L) fitted with a stirrer, cooling coil, thermometer, jacket and the like was charged with the starting material whose composition is shown in Table 4, purged with nitrogen, and subjected to a copolymerization for 48 hours with controlling the reaction temperature at 71° C. to 73° C. with stirring, whereby obtaining 5 types of the carrier particles, namely (g) to (k). The particle size and the surface sulfonic acid group amount of each resultant carrier particle were measured in the same manner as Example 1. The results are shown in Table 4. As a catalyst for the polymerization, aqueous solution of 0.5 g of potassium persulfate dissolved in 10 g of distilled water was employed.

[Preparation of Assay Reagent]

250 µl of aqueous solution which was adjusted at 10% (w/v) of the carrier particle (g) was placed in a 8 ml glass tube, to which then 170 µl of anti-human CRP goat serum (produced by DAKO, protein concentration: 18 mg/mL, also referred to as an antibody solution) was added, and allowed to be adsorbed with stirring for 1 hour at 37° C., and then combined with 2080 µl of BSA (bovine serum albumin)-containing glycine buffer (pH8.5), and the blocking treatment was effected with stirring for 60 minutes at 37° C. Then, an aliquot after the blocking treatment was placed in a 8 ml centrifugating tube, centrifuged at 18000 rpm for 60 minutes, removed the supernatant, redispersed in the BSA-containing glycine buffer (pH8.5), subjected twice to an excessive antibody treatment, combined with 2.5 ml of the BSA-containing glycine buffer (pH8.5), after ultrasonication, and then combined further with the BSA-containing glycine buffer (pH8.5) to make the final volume 5 ml, whereby preparing the assay reagent.

With preparing BSA-containing glycine buffer (pH8.5) so that the antibody sensitization amounts per surface area of the carrier particles (h), (i), (j) and (k) became similar, the assay reagents were prepared in a manner similar to that for the carrier particle (g). The centrifugation was conducted at 18000 rpm for 45 minutes for the carrier particle (h), at 15000 rpm for 30 minutes for the carrier particles (i) and (j) and at 18000 rpm for 60 minutes for the carrier particle (k).

EXAMPLE 12

Using the assay reagents consisting of the resultant carrier particles (i) and (j), the change in the absorbance observed upon measuring samples whose CRP concentration ranging from 0.5 to 30 mg/dl were determined under the conditions specified below.

Figure 9:
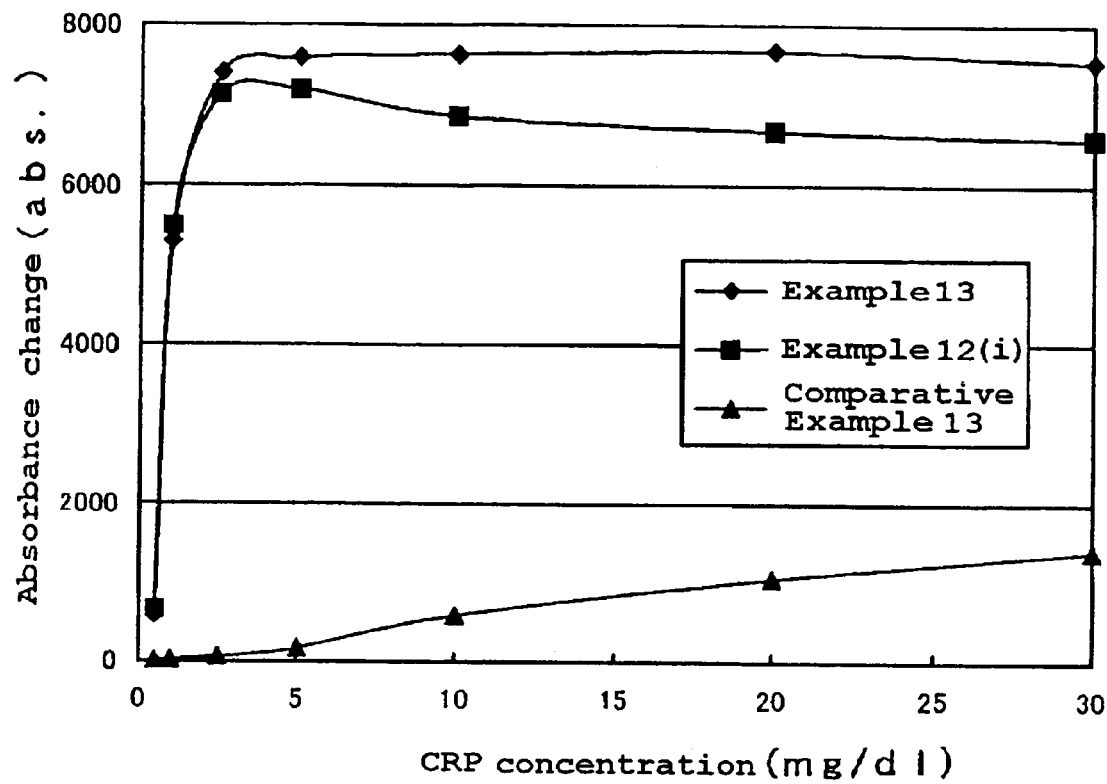
FIG. 9 shows the results of the assay of samples using the reagents prepared in Example 12 (i), Comparative Example 13 and Example 13.
Figure 10:
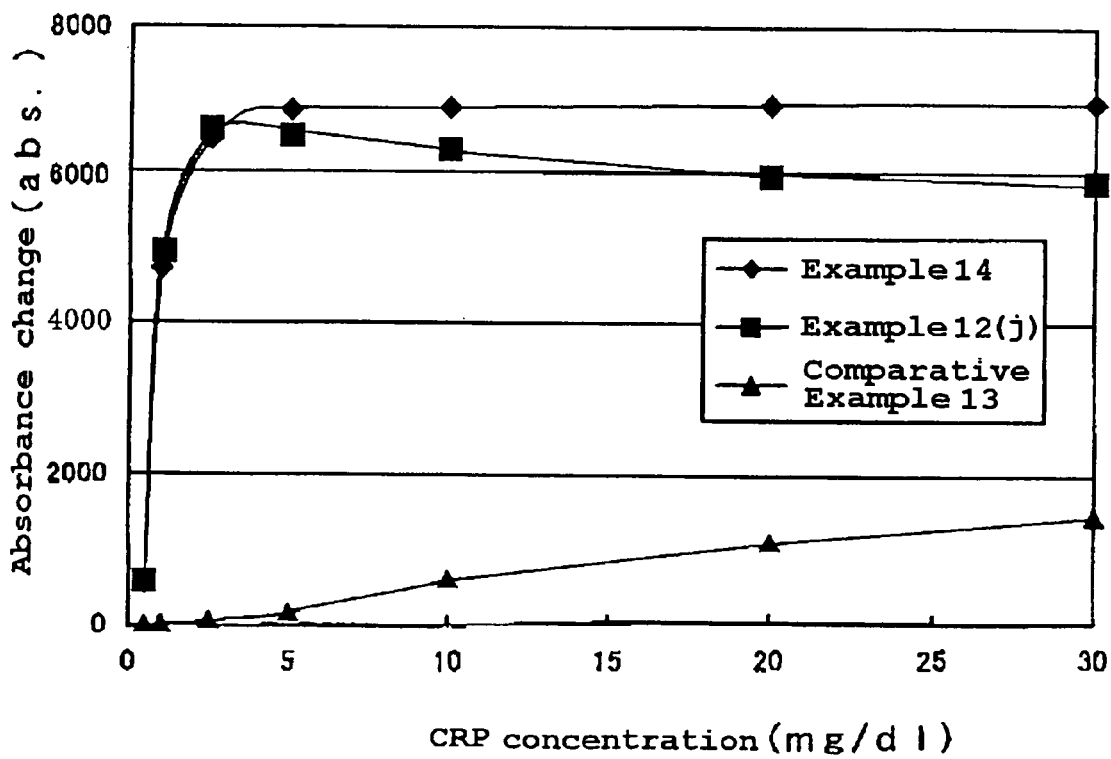
FIG. 10 shows the results of the assay of samples using the reagents prepared in Example 12 (j), Comparative Example 13 and Example 14.

The results are shown in FIG. 9 and FIG. 10.

Instrument: manufactured by HITACHI LTD, model 7150 automatic analyzer
Volumes: Sample: 3 µL
Diluent (R1): 270 µL (Composition of diluent: 1% by weight BSA-containing glycine buffer)
Assay reagent: 90 µL
Detection wavelength: 800 nm
Light observation point: 2 point-30-50p

COMPARATIVE EXAMPLE 13

Using an assay reagent containing of the resultant carrier particle (k), the change in the absorbance observed upon measuring samples whose CRP concentration ranging from 0.5 to 30 mg/dl were determined under the conditions similar to those in Example 12.

The results are shown in FIG. 9 and FIG. 10.

TABLE 4

| | Carrier particle | | | | |
| --- | --- | --- | --- | --- | --- |
| | (g) | (h) | (i) | (j) | (k) |
| Composition (g) | | | | | |
| Distilled water | 1600 | 1500 | 1500 | 1600 | 2300 |
| Styrene | 280 | 260 | 250 | 280 | 280 |
| Sodium styrene sulfonate | 3.0 | 0.9 | 0.78 | 3.5 | 5.0 |
| Average particle size (µm) | 0.049 | 0.118 | 0.402 | 0.409 | 0.052 |
| Surface sulfonic acid group amount (µmol/m$^2$) | 0.68 | 0.09 | 0.094 | 0.30 | 0.89 |

EXAMPLE 13

Using a mixture obtained by mixing an assay reagent containing of the resultant carrier particle (g) and an assay reagent containing of the resultant carrier particle (i) in the ratio of 1:10 as an assay reagent, the change in the absorbance observed upon measuring samples whose CRP concentration ranging from 0.5 to 30 mg/dl were determined under the conditions similar to those in Example 12.

The results are shown in FIG. 9.

EXAMPLE 14

Using a mixture obtained by mixing an assay reagent containing of the resultant carrier particle (h) and an assay reagent containing of the resultant carrier particle (j) in the ratio of 1:10 as an assay reagent, the change in the absorbance observed upon measuring samples whose CRP concentration ranging from 0.5 to 30 mg/dl were determined under the conditions similar to those in Example 12.

The results are shown in FIG. 10.

EXAMPLES 15 TO 18, COMPARATIVE EXAMPLES 14 TO 18

[Preparation of Carrier Particle]

A glass reaction vessel (2 L) fitted with a stirrer, cooling coil, thermometer, jacket and the like was charged with the starting material whose composition is shown in Table 5, further charged with aqueous solution of 0.5 g of potassium persulfate (initiator) dissolved in 10 g of distilled water, purged with nitrogen, and subjected to a copolymerization for 48 hours with controlling the reaction temperature at 71° C. to 73° C. with stirring.

The resultant carrier particle was filtered through a paper filter, examined for the particle size, and the average particle size and the CV value were calculated. The particle size was determined here using an image analyzer based on the image observed by a transmission electron microscope. The surface sulfonic acid group amount was determined in the same manner as Example 1.

[Preparation of Assay Reagent]

250 µl of aqueous solution adjusted at 10% (w/v) using the carrier particle obtained in Example 15 was placed in a 8 ml glass tube, to which then 170 µl of anti-human CRP goat serum (produced by DAKO, protein concentration: 18 mg/mL, also referred to as an antibody solution) was added, and allowed to be adsorbed with stirring for 1 hour at 37° C., and then combined with 2080 µl of BSA (bovine serum albumin)-containing glycine buffer (pH8.5), and the blocking treatment was effected with stirring for 60 minutes at 37° C. Then, an aliquot after the blocking treatment was placed in a 8 ml centrifugating tube, centrifuged at 18000 rpm for 60 minutes, removed the supernatant, redispersed in the BSA-containing glycine buffer (pH8.5), subjected twice to an excessive antibody treatment, combined with 2.5 ml of the BSA-containing glycine buffer (pH8.5), after ultrasonication, and then combined further with the BSA-containing glycine buffer (pH8.5) to make the final volume 5 ml, whereby preparing the assay reagent.

With preparing BSA-containing glycine buffer (pH8.5) so that the antibody sensitization amounts per surface area of the carrier particles produced in Examples 16 to 18 and Comparative Examples 14 to 18 became similar, the assay reagents were prepared in the same manner as Example 15.

The centrifugation was conducted at 18000 rpm for 60 minutes in Example 15 and Comparative Example 18, and at 18000 rpm for 70 minutes in Examples 16 and 17 and Comparative Examples 16 and 17.

[Evaluation of Assay Reagent Performance]

Using each of the resultant assay reagents, the change in the absorbance observed upon measuring samples whose CRP concentration ranging from 0.5 to 30 mg/dl were determined under the conditions specified below.

Figure 11:
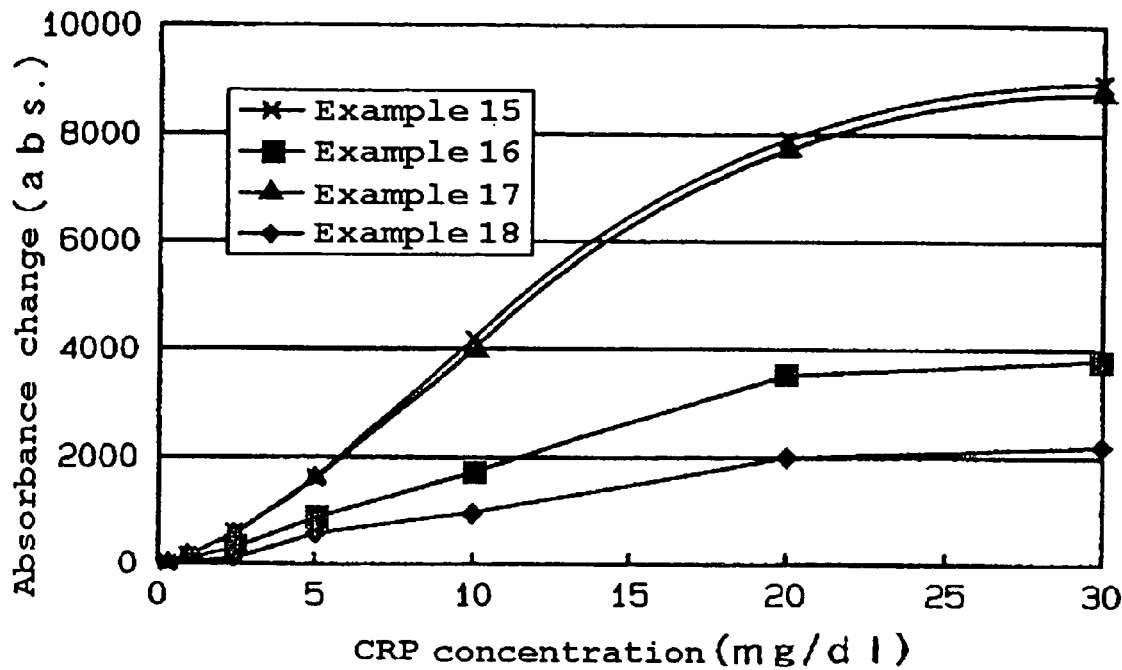
FIG. 11 shows the results of the assay of samples using the reagents prepared in Examples 15 to 18.
Figure 12:
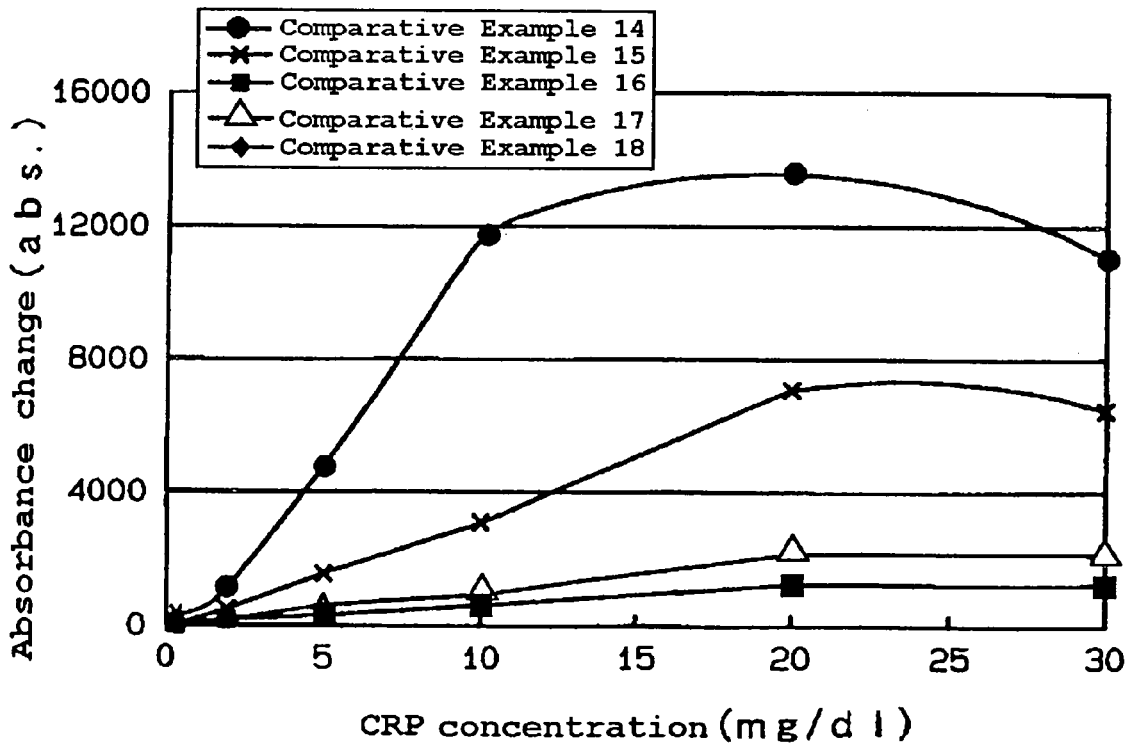
FIG. 12 shows the results of the assay of samples using the reagents prepared in Examples 14 to 18.

The results are shown in FIG. 11 and FIG. 12.

Instrument: manufactured by HITACHI LTD, model 7150 automatic analyzer

Volumes: Sample: 3 µL

Diluent (R1): 270 µL (Composition of diluent: 1% by weight BSA-containing glycine buffer)

Assay reagent: 90 µL

Detection wavelength: 800 nm

Light observation point: 2 point-30-50p

TABLE 5

|  | Example15 | Example16 | Example17 | Example18 | Comparative Example14 | Comparative Example15 | Comparative Example16 | Comparative Example17 | Comparative Example18 |
|---|---|---|---|---|---|---|---|---|---|
| Composition (g) | | | | | | | | | |
| Distilled water | 1500 | 1500 | 1600 | 2000 | 2300 | 1600 | 1600 | 2200 | 1500 |
| Styrene | 260 | 260 | 280 | 280 | 280 | 280 | 280 | 260 | 250 |
| Sodium styrene sulfonate | 3.1 | 2.7 | 2.4 | 2.5 | 3.0 | 3.3 | 3.0 | 2.25 | 2.6 |
| Average particle size (µm) | 0.045 | 0.075 | 0.095 | 0.091 | 0.049 | 0.048 | 0.079 | 0.098 | 0.120 |
| CVvalue(%) | 12.68 | 15.49 | 8.49 | 18.17 | 7.25 | 21.04 | 6.04 | 5.49 | 7.58 |
| Surface sulfonic acid group amount (µmol/m$^2$) | 0.683 | 0.516 | 0.458 | 0.462 | 0.680 | 0.689 | 0.519 | 0.451 | 0.472 |

INDUSTRIAL APPLICABILITY

According to the invention, a carrier particle latex for an assay reagent capable of assaying a biological sample at awide range of the concentration in an immunoserological test and capable of being stored stably for a prolonged period and an assay reagent employing the same are provided.

The invention claimed is:

1. A carrier particle latex for an assay reagent comprising a carrier particle consisting essentially of a copolymer consisting of only a polymerizable monomer having a phenyl group and a polymerizable monomer having a phenyl group and a sulfonate, as monomer components, wherein said carrier particle has a surface sulfonic acid group amount of 0.005 to 0.7 μmol/m$^2$ and an average particle size of 0.01 to 1.5 μm.

2. The carrier particle latex for an assay reagent according to claim 1, which contains substantially no emulsifier.

3. The carrier particle latex for an assay reagent according to claim 1, wherein the polymerizable monomer having the phenyl group is styrene and the polymerizable monomer having the phenyl group and a sulfonate is styrene sulfonate.

4. An assay reagent, wherein a substance specifically binding to an analyte is supported on the carrier particle of a carrier particle latex for an assay reagent according to claim 1.

* * * * *

UNITED STATES PATENT AND TRADEMARK OFFICE
CERTIFICATE OF CORRECTION

| | | |
|---|---|---|
| PATENT NO. | : 7,338,813 B2 | Page 1 of 1 |
| APPLICATION NO. | : 10/482302 | |
| DATED | : March 4, 2008 | |
| INVENTOR(S) | : Satoshi Obana | |

It is certified that error appears in the above-identified patent and that said Letters Patent is hereby corrected as shown below:

On the Title Page
Item (56) References Cited, FOREIGN PATENT DOCUMENTS the following is incorrectly cited:

| JP | 55131008 | B2 | 10/1980 |
| JP | 58198508 | B2 | 11/1983 |
| JP | 63065369 | B2 | 3/1988 |

The following should replace the incorrectly cited references:

| JP | 58050645 | B2 | 11/1983 |
| JP | 01036484 | B2 | 8/1989 |
| JP | 2588174 | B2 | 12/1996 |

Signed and Sealed this

Twenty-ninth Day of July, 2008

JON W. DUDAS
*Director of the United States Patent and Trademark Office*